United States Patent [19]

Toy

[11] 4,112,356

[45] Sep. 5, 1978

[54] SEMICONDUCTOR GAS DETECTOR CIRCUIT

[76] Inventor: Stephen M. Toy, 4190 Manuela Ave., Palo Alto, Calif. 94306

[21] Appl. No.: 752,413

[22] Filed: Dec. 20, 1976

[51] Int. Cl.² .............................................. G01N 27/00

[52] U.S. Cl. .............................. 324/71 SN; 324/65 R; 73/27 R; 340/634

[58] Field of Search ......................... 324/71 SN, 64 R; 73/27 R; 340/237 R, 237 S

[56] References Cited

U.S. PATENT DOCUMENTS

| | | | |
|---|---|---|---|
| 3,482,233 | 12/1969 | Ogg | 340/237 R |
| 3,820,398 | 6/1974 | Rekai | 324/65 R X |
| 3,937,061 | 2/1976 | Rhodes, Jr. | 73/27 R |
| 3,961,247 | 6/1976 | Toke | 324/65 R |
| 3,997,837 | 12/1976 | Betz et al. | 324/71 SN |

*Primary Examiner*—Stanley T. Krawczewicz
*Assistant Examiner*—Vincent J. Sunderdick
*Attorney, Agent, or Firm*—Harry E. Aine; Harvey G. Lowhurst

[57] ABSTRACT

In a gas detector circuit a semiconductive detector, such as a Taguchi detector, is disposed in gas communication with the gas to be detected. The detector has a sensing resistor incorporated therein with a value of resistance that changes in accordance with the concentration of the gas constituent being detected. This type of detector provides an output signal with a temperature dependence caused by the temperature coefficient of the resistance of the resistive detector with a negative sign. The temperature dependent output signal derived from the detector is fed to one input of a differential amplifier for comparison against a second input to derive an output signal which is fed to an alarm and/or meter and/or recorder. A feedback signal portion of the output of the differential amplifier is fed back to the second input of the differential amplifier, as a feedback component of the second input, via the intermediary of a gain control resistor. The supply current drawn by the differential amplifier has a positive temperature coefficient and the supply current is passed through a resistor to derive a correction voltage which is superimposed on the feedback voltage of the differential amplifier to compensate for the temperature coefficient of the semiconductive detector.

11 Claims, 3 Drawing Figures

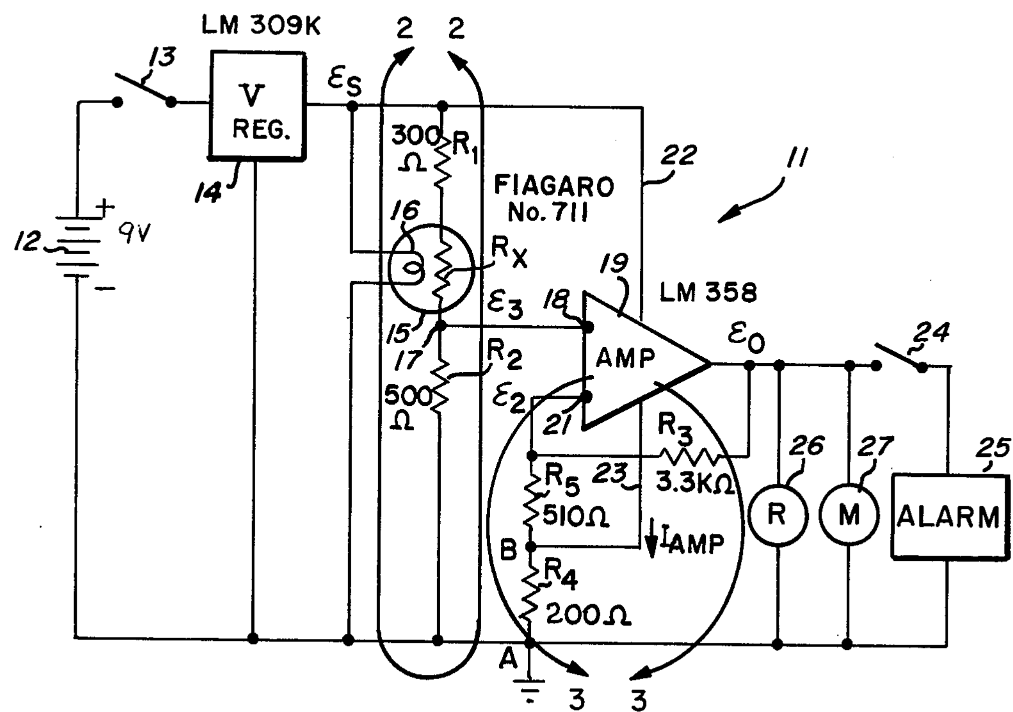
Fig_1
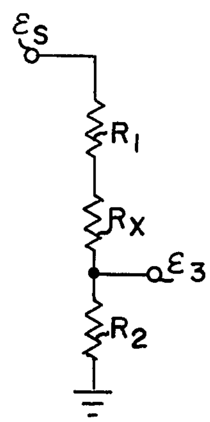
Fig_2
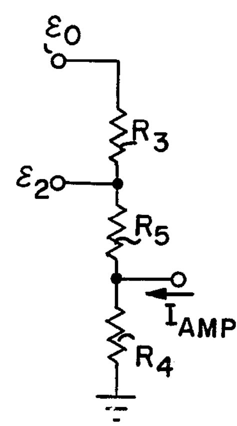
Fig_3

SEMICONDUCTOR GAS DETECTOR CIRCUIT

BACKGROUND OF THE INVENTION

The present invention relates in general to semiconductor gas detector circuits and more particularly to such circuits employing temperature compensation for compensating the temperature coefficient of the semiconductor detector.

DESCRIPTION OF THE PRIOR ART

Heretofore, semiconductor gas detector circuits have been proposed which have employed means for compensating for the temperature coefficient of the semiconductor gas detector. A typical example of such a prior art gas detector circuit is found in U.S. Pat. No. 3,932,807 issued Jan. 13, 1976.

One of the problems with these prior semiconductor detector circuits is that they are relatively complicated requiring a number of electrical bridges and the like to effect temperature compensation. For example, in the aforecited patent the electrical heater for the semiconductive gas detector element is incorporated in a bridge circuit and the current supplied to the bridge circuit is automatically controlled in response to variations of the out of balance voltage of the bridge circuit so as to maintain constancy of the resistance of the heating element and hence of its operating temperature.

While these aforementioned temperature compensation schemes serve to provide some degree of temperature compensation they are relatively complicated and it is desired to provide a simplified temperature compensation network.

SUMMARY OF THE PRESENT INVENTION

The principal object of the present invention is the provision of an improved semiconductor gas detector circuit having simplified temperature compensation.

In one feature of the present invention, the negative temperature coefficient of resistance of the semiconductor gas detector is compensated by employing an output derived upon the positive temperature coefficient of the supply current drawn by the differential amplifier employed to amplify the output signal derived from the semiconductive detector, whereby the complexity of the temperature compensation circuitry is substantially reduced.

In another feature of the present invention, the value of a resistor series connected with the semiconductive resistive sensor to be compensated and across which the sensing input signal to a differential amplifier is derived, is chosen relative to the value of a second resistor in the input circuit to the other input of the differential amplifier, and across which the current supplied to the differential amplifier is drawn, so that the ratio of the first and second resistors are arranged to compensate for the negative temperature coefficient of resistance of the semiconductor gas detector.

Other features and advantages of the present invention will become apparent upon a perusal of the following specification taken in connection with the accompanying drawings wherein:

BRIEF DESCRIPTION OF THE DRAWING

FIG. 1 is a schematic circuit diagram, partly in block diagram form, of a semiconductor gas detector circuit incorporating features of the present invention, FIG. 2 is a schematic simplified circuit diagram of a portion of the structure of FIG. 1 delineated by line 2—2, and FIG. 3 is a simplified schematic circuit diagram for a portion of the circuit of FIG. 1 delineated by line 3—3.

DESCRIPTION OF THE PREFERRED EMBODIMENTS

Referring now to FIG. 1 there is shown a semiconductor gas detector circuit 11 incorporating features of the present invention. The circuit 11 includes a source of voltage 12, such as a nine volt composite battery comprising six 1.5 volt C battery cells. The output of the battery 12 is applied via a first switch 13 to the input of a voltage regulator 14 such as a LM 309K regulator producing a five volt regulated output $\epsilon_s$.

The regulated output voltage $\epsilon_s$ is applied across a first voltage divider network consisting of resistors $R_1$, $R_x$ (the sensing resistor of a semiconductive gas detector sensor such as a Fiagaro Model No. 711 of the Taguchi type) and a second voltage divider resistor $R_2$. In a typical example $R_1$ has a value of 300 ohms, $R_2$ has a value of 500 ohms and the value of $R_x$ is much, much greater than either $R_1$ or $R_2$.

The semiconductive gas sensor 15 includes a heating element 16 which serves to heat the sensing resistor $R_x$ of the sensor 15 to its operating temperature. The heating element 16 is connected across the output of the voltage regulator 14 for supplying operating current thereto.

As the concentration of the gas constituent of interest, and which is to be detected, varies the resistance $R_x$ varies to produce a change in an output voltage $\epsilon_3$ derived from a sensing node 17 of the voltage divider disposed between resistor $R_x$ and $R_2$. The sensor output voltage $\epsilon_3$ is fed to one input terminal 18 of a differential amplifier 19 such as a LM 358. A portion of the output voltage $\epsilon_0$ derived from the output of the differential amplifier 19 is fed back to the other input 21 of the differential amplifier 19 via the intermediary of a gain control resistor $R_3$ as of 3.3 kilohms. The gain control feedback resistor $R_3$ serves to control the sensitivity of the gas detector circuit.

A second voltage divider network consisting of a series connection of resistors $R_3$, and $R_4$ is connected between the second input terminal 21 of the differential amplifier and ground which is the negative terminal of the battery 12. In a typical example, $R_5$ has a value of 510 ohms and $R_4$ has a value 200 ohms. Current is supplied to the differential amplifier 19 from the output of the voltage regulator 14 via line 22. The current supplied to the differential amplifier flows through the differential amplifier and back to the battery 12 via output line 23 and resistor $R_4$ of the second voltage divider network.

It turns out that the sensing resistor $R_x$ of the semiconductor sensor 15 has a negative temperature coefficient which makes the sensor output signal $\epsilon_3$ temperature dependent and it is desired to compensate for this temperature dependence. It also turns out that the current supplied through the differential amplifier 19 has a positive temperature coefficient. Thus by arranging the ratio of the values of the resistance of resistor $R_2$ to the value of the resistance of resistor $R_4$ to the proper value, the first order temperature dependence of the output voltage $\epsilon_3$ can be compensated. In the circuit of FIG. 1, utilizing the values of resistance indicated, a value for $R_4$ of 200 ohms and a value of $R_2$ of 500 ohms temperature compensates the gas detector circuit.

The output voltage $\epsilon_3$ is fed via a switch 24 to an alarm or sounder 25 for sounding an alarm when the concentration of the gas constituent of interest exceeds a predetermined value determined by the threshold setting of the alarm 25. In addition, a recorder 26 and a meter 27 can be connected between the output voltage $\epsilon_0$ and ground for recording and metering, respectively, the output signal $\epsilon_0$.

DERIVATION OF THE TEMPERATURE COMPENSATION

Referring now to FIGS. 2 and 3 there is shown, in simplified circuit diagram form, the voltage divider network portions of the circuit of FIG. 1 delineated by lines 2—2 and 3—3, respectively.

$$\epsilon_3 = \epsilon_s \frac{R_2}{R_1 + R_x + R_2} \quad \text{Eq. (1)}$$

since $R_x >> R_1, R_2$ we find:

$$\epsilon_3 \cong \epsilon_s \frac{R_2}{R_x} \quad \text{Eq. (2)}$$

$$\epsilon_2 = \epsilon_0 \frac{R_4 + R_5}{R_3 + R_5 + R_4} + \frac{I_{amp} R_3 R_4}{R_5 + R_4 + R_3} \quad \text{Eq. (3)}$$

since $R_3 >> R_4, R_5$ we find:

$$\epsilon_2 \cong \epsilon_0 \frac{R_4 + R_5}{R_3} + I_{amp} R_4 \quad \text{Eq. (4)}$$

Since the differential amplifier has very high open loop gain, $\epsilon_2 \cong \epsilon_3$, and therefore:

$$\epsilon_s \frac{R_2}{R_x} \cong \epsilon_0 \frac{R_4 + R_5}{R_3} + I_{amp} R_4 \quad \text{Eq. (5)}$$

and $$\epsilon_0 = \epsilon_s \frac{R_3}{R_x} \cdot \frac{R_2}{R_4 + R_5} - I_{amp} \frac{R_3 R_4}{R_4 + R_5} \quad \text{Eq. (6)}$$

Equation (6) determines the output sensitivity. If it is desired that output voltage be independent of temperature, and both $R_x$ and $I_{amp}$ depend upon temperature, we require:

$$\frac{d\epsilon_0}{dT} = \epsilon_s \frac{R_3 R_2}{R_4 + R_5} \frac{d}{dT}\left(\frac{1}{R_x}\right) - \frac{R_3 R_4}{R_4 + R_5} \frac{dI_{amp}}{dT} = 0 \quad \text{Eq. (7)}$$

or $$\frac{\epsilon_s R_2}{\epsilon R_4}\left(\frac{1}{R_x}\right)^2 \frac{dR_x}{dT} + \frac{dI_{amp}}{dT} = 0 \quad \text{Eq. (8)}$$

Since $$\frac{dI_{amp}}{dT}$$

is positive and $$\frac{dR_x}{dT}$$

is negative, for given values of $\epsilon_s$ and $R_x$ a proper choice of the ratio $$\frac{R_2}{R_4}$$

can eliminate the first order temperature dependence of the output voltage. The desired output sensitivity can still be obtained by the proper selection of the value of $R_3$.

The advantage of the semiconductor gas detecting circuit 11 of the present invention is that it greatly simplifies the temperature compensation circuitry employed in semiconductor gas detector circuits.

What is claim is:

1. In a semiconductive gas detector circuit:

semiconductive gas detector means disposed in gas communication with a gas to be detected and having a sensing resistor means with a value of resistance which varies in accordance with the concentration of the gas constituent to be detected and also having a temperature coefficient of resistance of a first polarity;

second resistor means series connected with said sensing resistor means to form a voltage divider network therewith which is to be connected across a source of voltage and having an output node connected intermediate said sensing and second resistor means on which is established a first output signal which varies in accordance with the concentration of the detected gas constituent and which has a temperature dependence;

differential amplifier means having first and second signal input terminals, an output signal terminal and a pair of power supply terminals, for supplying a flow of current through said differential amplifier means, the value of supply current having a temperature coefficient of current of a second polarity opposite to that of said first polarity, means for coupling said first output signal into said first input terminal of said differential amplifier means;

third and fourth resistor means series connected to form a second voltage divider network and being connected across the output of said differential amplifier means for voltage dividing thereacross the output signal of said differential amplifier means and having a feedback signal node between said third resistor means and said fourth resistor means on which to derive a feedback signal which varies as the output signal, a supply current node disposed between said fourth resistor means and said third resistor means, means for applying the supply current of said differential amplifier means through said fourth resistor means, to derive a temperature compensation feedback signal component of said feedback signal and means for coupling said feedback component signal into said second input terminal of said differential amplifier means; and the ratio of the resistance value of said second resistor means to that of said fourth resistor means being such as to compensate for the temperature dependence of said first output signal.

2. The apparatus of claim 1 wherein the temperature coefficient of resistance of said sensing resistor means is of negative sign and said temperature coefficient of current of said differential amplifier means is of positive sign.

3. The apparatus of claim 1 wherein said ratio of the values of resistance fall within the range of 1.5 to 4.0.

4. The apparatus of claim 1 including alarm means for alarming the user when the concentration of the detected gas constituent exceeds a certain predetermined value and means for coupling said alarm means to said output signal of said differential amplifier means to be responsive thereto.

5. The apparatus of claim 1 including meter means for metering the concentration of the detected gas constituent and means for coupling said meter means to said output signal of said differential amplifier means to be responsive thereto.

6. The apparatus of claim 1 including recorder means for recording the concentration of the detected gas constituent and means for coupling said recorder means to said output signal of said differential amplifier means to be responsive thereto.

7. The apparatus of claim 1 wherein the value of resistance of said third resistor means is greater than the value of resistance of said fourth resistor means.

8. The apparatus of claim 1 wherein the value of resistance of said sensing resistor means is greater than the value of resistance of said second resistor means.

9. The apparatus of claim 1 including voltage regulator means for supplying a regulated output voltage, and means for coupling said regulated output voltage across said first voltage divider network.

10. The apparatus of claim 1 including fifth resistor means connected in said second voltage divider network between said third and fourth resistor means and wherein said supply current node is between said fourth and fifth resistor means.

11. In a gas detector circuit:

semiconductor gas detector means disposed in gas communication with a gas to be detected and having a sensing resistor means with a value of resistance which varies in accordance with the concentration of the gas constituent to be detected in the gas communicating with said detector means and also having a temperature coefficient of resistance of a first polarity;

differential amplifier means having a first input terminal responsive to an output signal derived from said semiconductive gas detector means, such output signal of said semiconductive gas detector means having a temperature dependence derived from the temperature coefficient of said sensing resistor means;

means for coupling the output signal of said differential amplifier means back to a second input terminal of said differential amplifier means so that the differential amplifier means is responsive to the difference of the feedback signal and of the sensor signal to derive the output signal;

means for feeding a supply current through said differential amplifier means, said supply current having a temperature coefficient of a second polarity; and means responsive to the supply current fed through said differential amplifier means for deriving a temperature compensating signal, and means for feeding the temperature compensating signal into an input of said differential amplifier means for compensating for the temperature coefficient of resistance of said sensing resistor means of said semiconductive gas detector means.

* * * * *